United States Patent [19]

Baier

[11] Patent Number: 4,484,585
[45] Date of Patent: Nov. 27, 1984

[54] CATHETERS

[75] Inventor: Manfred Baier, Bretten-Diedelsheim, Fed. Rep. of Germany

[73] Assignee: Richard Wolf GmbH, Knittlingen, Fed. Rep. of Germany

[21] Appl. No.: 414,299

[22] Filed: Sep. 2, 1982

[30] Foreign Application Priority Data

Sep. 12, 1981 [DE] Fed. Rep. of Germany ... 8126671[U]

[51] Int. Cl.³ .................... A61M 25/00; A61B 5/10
[52] U.S. Cl. ................................ 128/748; 604/280
[58] Field of Search ............. 128/748, 774, 778, 780; 604/43–45, 280

[56] References Cited

U.S. PATENT DOCUMENTS

| 1,696,018 | 12/1928 | Schellberg | 604/43 |
| 3,480,003 | 11/1969 | Crites | 128/780 |
| 3,939,823 | 2/1976 | Kaye et al. | 128/748 |

OTHER PUBLICATIONS

Ulmsten et al, Electromedica, 1980, vol. 48 pp. 9–12.
Ghoneim et al, Urology, May 1975, vol. V, No. 5, pp. 632–637.

Primary Examiner—Dalton L. Truluck
Attorney, Agent, or Firm—Kinzer, Plyer, Dorn & McEachran

[57] ABSTRACT

This invention relates to catheters for measuring the pressure along the length of a patient's urethra, of the kind having a closed distal end and provided at a distance from said distal end with a lateral outlet for a fluid to be fed in at a constant rate of flow through a passage arranged for connection to a measuring instrument.

According to the invention, the lateral catheter outlet is formed by an annular gap extending in a plane at right angles to the longitudinal axis of the catheter and into which opens the supply passage for the fluid.

Advantageously, the catheter is transversely divided into two parts constituting distal and proximal sections having mutually opposed terminal areas. These terminal areas are connected by a rigid bridging member to form the annular gap, which latter for example has a width of advantageously between 0.2 and 0.5 mm.

7 Claims, 8 Drawing Figures

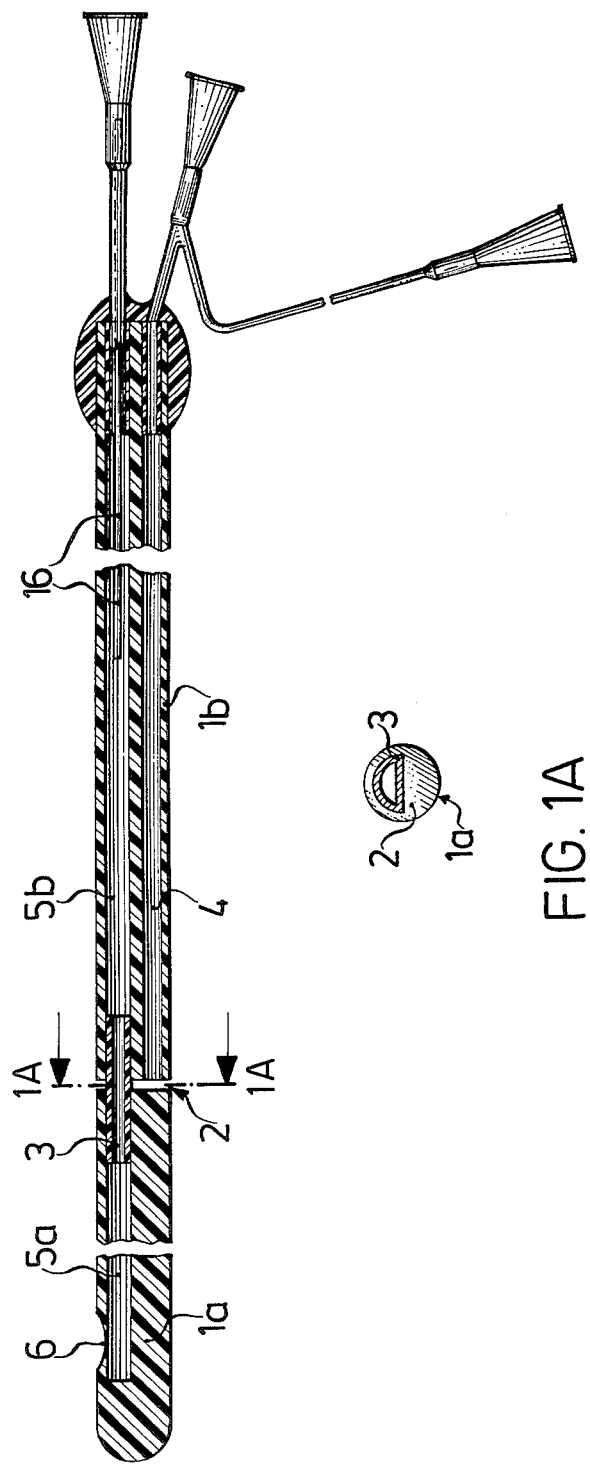

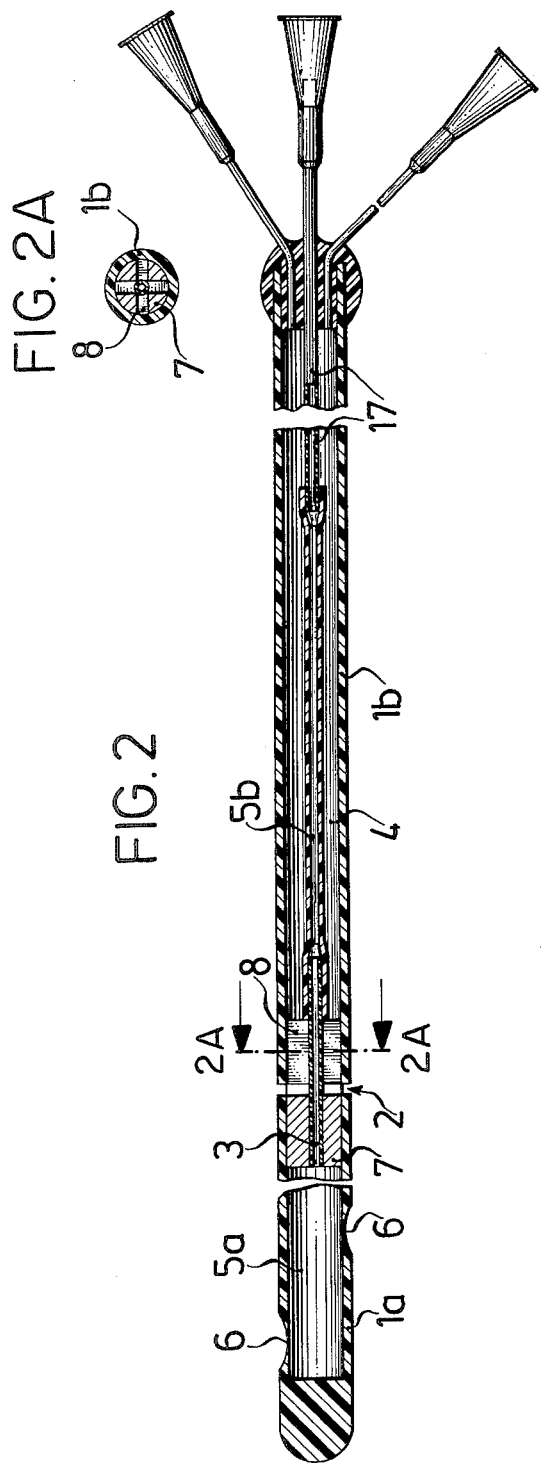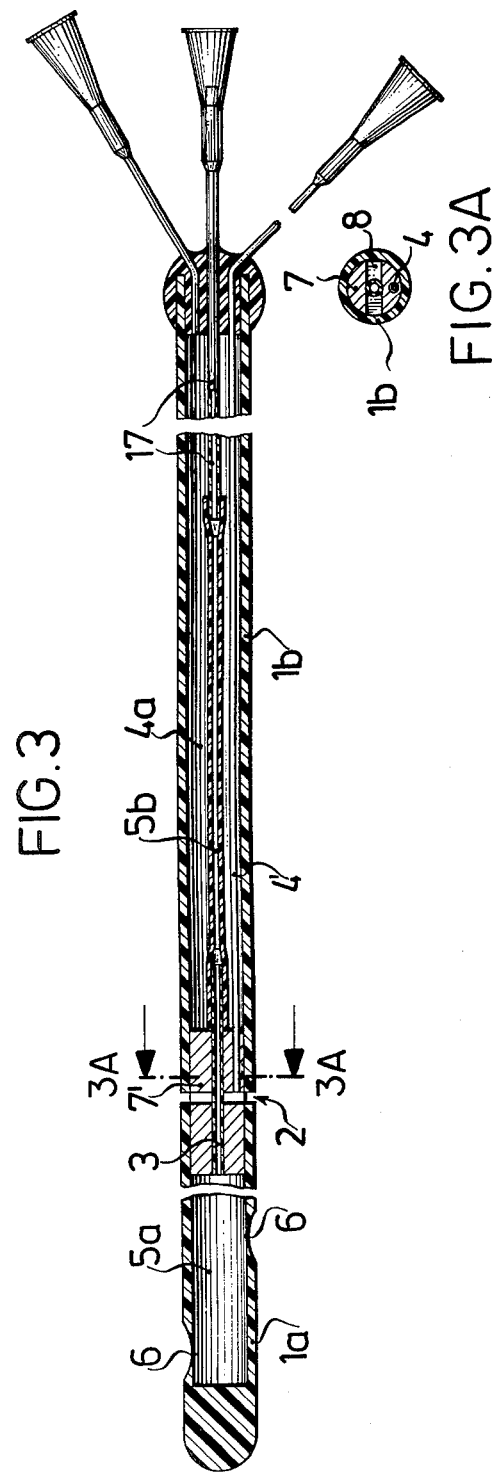

CATHETERS

BACKGROUND OF THE INVENTION

The present invention relates to catheters for measuring urethral pressure, along the length of the urethra, which is provided at a distance from the closed distal extremity with a lateral outlet for a fluid fed in at a constant rate of flow through a passage arranged for connection to a measuring instrument.

To be able to reach a diagnosis in the case where urinary incontinence occurs, use is made of urethrometers for measuring the urethral pressure gradient, which utilise a catheter which has one or two circular lateral wall perforations in the area of the distal end. A fluid is fed to the wall perforation or perforations at a constant rate of flow by a pump, through the catheter connected at the proximal end to a pressure gauge, said fluid undergoing a pressure rise and exerting said pressure through the wall perforation on the surface of the urethra surrounding the catheter, until this back-up pressure becomes a little higher than the back pressure of the urethra and fluid consequently issues from the catheter through the perforations. This back-up pressure is recorded as a graph by the measuring instrument at mensuration points along the length of the urethra, whilst the catheter is drawn out of the urethra at as uniform a speed as possible.

It has been observed that no precise measurement of actual back or back-up pressure against the urethra is possible with a catheter of the kind hereinabove referred to, since the back pressure is measured practically only in punctiform manner along the length of the urethra and since no unequivocal co-ordination is possible between the momentary pressure value and the point of measurement.

It is therefore an object of the invention to provide a catheter for securing precise measurements of the actual back pressure against the urethra.

SUMMARY OF THE INVENTION

To achieve this and other objects, in a catheter for measuring the pressure along the length of a patient's urethra, of the kind having a closed distal end and provided at a distance from said distal end with a lateral outlet for a fluid to be fed in at a constant rate of flow through a passage arranged for connection to a measuring instrument, the invention consists in that said lateral catheter outlet is formed by an annular gap extending in a plane at right angles to the longitudinal axis of the catheter, and into which opens the supply passage for the fluid.

To obtain this annular gap, the catheter is transversely divided into two parts constituting distal and proximal sections having mutually opposed terminal areas, said terminal areas being connected by a rigid bridging member to form said annular gap. The width of said gap advantageously amounts to between 0.2 and 0.5 mm depending on the fluid utilised.

It is advantageous furthermore to be able to measure the patient's bladder pressure apart from measuring the back pressure at points of measurement distributed along the length of the urethra. This is accomplished by making the rigid bridging member as a tubular element which connects mensuration passages extending respectively through both catheter areas, the distal end of one passage having at least one lateral catheter perforation, and the proximal end of the other mensuration passage being arranged for connection to an instrument for measuring the pressure of the patient's bladder.

BRIEF DESCRIPTION OF THE DRAWINGS

In order that the invention may be more clearly understood, reference will now be made to the accompanying drawings, which show certain embodiments thereof by way of example and in which:

FIG. 1 is a longitudinal cross section through a catheter having passages for measuring the back pressure and the bladder pressure.

FIG. 1a is a section taken along line 1a—1a of FIG. 1.

FIG. 2 is a longitudinal cross section through a catheter having passages for measuring the back pressure and the bladder pressure.

FIG. 2a is a section taken along line 2a—2a of FIG. 2.

FIG. 3 is a longitudinal cross section through a catheter having passages for measuring the back pressure and the bladder pressure.

FIG. 3a is a section taken along line 3a—3a in FIG. 3.

DETAILED DESCRIPTION OF PREFERRED EMBODIMENTS

Figures 4, 4A:
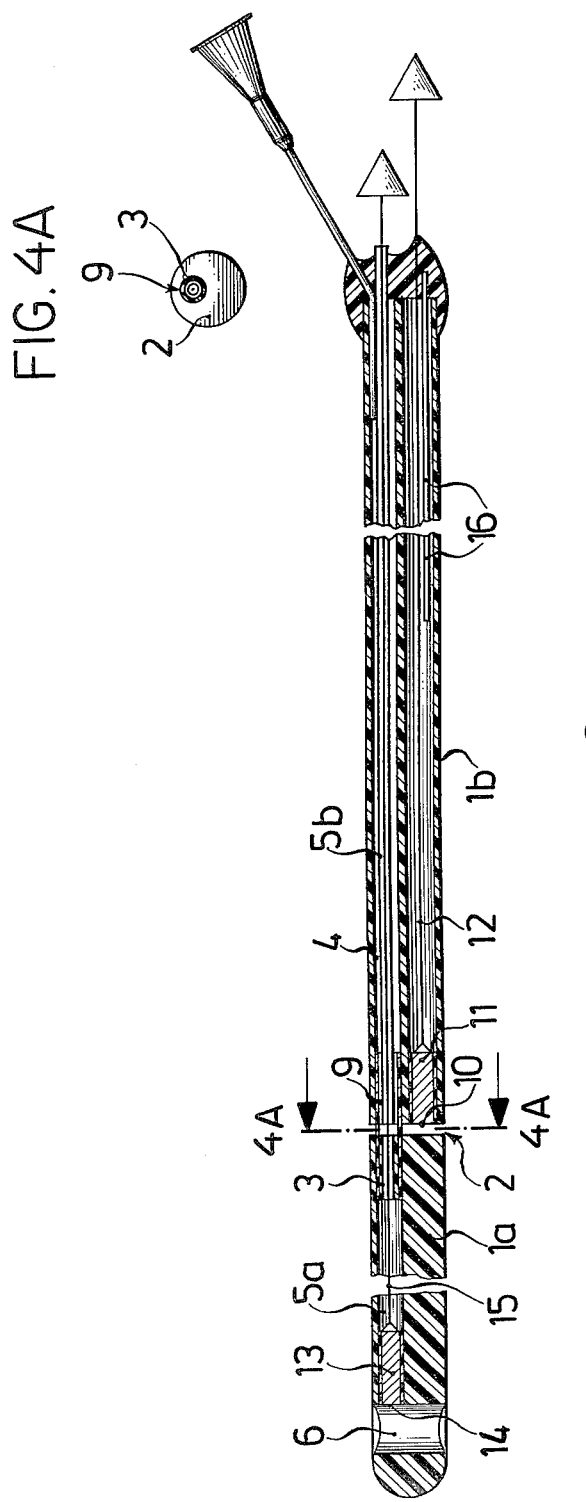
FIG. 4 shows a longitudinal cross section through a catheter comprising a mensuration device for measuring the back and bladder pressures.
FIG. 4a is a section taken along 4a—4a of FIG. 4.

Referring now to the drawings there is shown a catheter, the barrel of which is transversely divided into two parts constituting distal and proximal sections 1a and 1b respectively. In practice the distal section 1a is about 6 cm long. Between the mutually opposed terminal areas of these two sections there is an interconnecting bridging member 3 the ends of which project into the two sections in such a manner as to define an annular gap between them, which advantageously has an axial length of between about 0.2 mm and 0.5 mm depending on the nature of the fluid.

A passage 4 extending through the proximal catheter section opens into the annular gap 2 at its distal end. The proximal end of this section is connected to a fluid pump and to a pressure measuring instrument. The fluid, e.g. water, is fed to the annular gap 2 at a constant rate of flow as soon as the catheter has been inserted into the patient's urethra which latter fits tightly around the catheter. Due to the infeed of fluid, a back pressure builds up in the annular gap 2, which acts on the wall of the urethra until this wall yields and fluid is able to emerge. This back pressure is measured via the passage 4 at successive mensuration points along the length of the urethra whilst withdrawing the catheter, and plotted as a graph which provides the physician with an aid in arriving at a diagnosis.

The catheter is advantageously constructed in such manner that the patient's bladder pressure may also be measured. For this purpose, the rigid connecting bridging member 3 is formed as a tubular element which connects a mensuration passage 5a in the distal longitudinal section 1a and a mensuration passage 5b in the proximal longitudinal section 1b. The passage 5a is connectable to the bladder via a catheter wall perforation 6 and the passage 5b is connected to an instrument for measuring the pressure in the bladder.

The construction described enables the back pressure exerted on the urethra to be precisely detectable throughout the periphery of the annular gap 2 at all mensuration points along the length of the urethra, and the bladder pressure may complementarily be determined.

According to FIG. 2, the mensuration passages 5a, 5b are centrally located, so that they are surrounded by the passage 4 which then opens at the distal end via a support 7 for the tubular bridging member 3 and situated before the annular gap 2, into the annular gap 2 through cruciformly arranged passages 8, which establish the connection to the pressure measuring instrument.

According to FIG. 3, a support 7 similar to that shown in FIG. 2, is provided for the rigid bridging member 3, through which extends the distal extremity of the perfusion passage 4 leading into the annular gap 2, the support 7 again having passages 8 which connect the annular gap 2 to the pressure measuring instrument via the passage 4.

In FIGS. 2 and 3, the mensuration passage 5a is connected to the contents of the bladder via two wall perforations 6 of the catheter.

According to FIG. 4, the rigid bridging member 3 connecting the two catheter sections 1a and 1b is provided across the width of the annular gap 2 and across the length of the tubular bridge supported in section 1b with a wall perforation 9 which connects the annular gap 2 to the passage 4 for infeed of the fluid into the annular gap 2. At the proximal end, the end surface 10 of a pressure sensor 11 which is connected by a conductor 12 to a corresponding measuring instrument for determining the back pressure within the annular gap, terminates at the surface delimiting the annular gap.

Also provided for measuring the bladder pressure is a pressure sensor 13 which terminates the passage 5a and the end surface 14 of which is located adjacent the lateral wall perforation 6 of the catheter and facing towards it. The pressure sensor 13 is connected by a conductor 15 extending through the passages 5a, 5b to a measuring instrument for determining the bladder pressure.

In all the examples illustrated, the catheter may be stabilised at the proximal end by a rigid rod 16 (FIGS. 1 and 4) or by means of rigid tubular elements 17 (FIGS. 2 and 3).

Since the back pressure is a little lower within the annular gap 2 than the back pressure in the perfusion and measuring passage 4 (FIGS. 1 and 2) a mensuration error may intervene, but this may be eliminated in simple manner by providing a separate perfusion passage which opens into the annular gap 2.

The measuring instruments hereinabove referred to have not been illustrated since they per se form no part of the invention and are conventional or as desired.

I claim:

1. In a catheter for measuring the pressure along the length of a patient's urethra, of the kind having a closed distal end and provided at a distance from said distal end with a lateral outlet for a fluid to be fed in at a constant rate of flow through a passage arranged for connection to a measuring instrument, the invention which consists in that said lateral catheter outlet is formed by an annular gap extending in a plane at right angles to the longitudinal axis of said catheter and into which opens said supply passage for the fluid.

2. A catheter according to claim 1, which is transversely divided into two parts constituting distal and proximal sections having mutually opposed terminal areas, said terminal areas being connected by a rigid bridging member to form said annular gap, said annular gap between said two sections having an axial length of between 0.2 and 0.5 mm.

3. A catheter according to claim 2, wherein each said catheter section is provided with a mensuration passage, and said bridging member is constituted by a tubular element which connects said mensuration passages, the distal end of said mensuration passage in said distal catheter section having at least one lateral catheter perforation and the proximal end of said mensuration passage in said proximal catheter section being arranged for connection to an instrument for measuring the pressure of a patient's bladder.

4. A catheter according to claim 2, wherein a pressure sensor for detecting the pressure in said annular gap has an end surface which terminates at the distal end of said proximal catheter section, said pressure sensor being arranged for connection to a measuring instrument via a conductor extending longitudinally of said proximal catheter section.

5. A catheter according to claim 3, wherein said mensuration passage in said distal catheter section is shut off for measuring bladder pressure by means of a pressure sensor having an end surface located adjacent said lateral catheter perforation.

6. A catheter according to claim 3, wherein a pressure sensor for detecting the pressure in said annular gap has an end surface which terminates at the distal end of said proximal catheter section, said pressure sensor being arranged for connection to a measuring instrument via a conductor extending longitudinally of said proximal catheter section.

7. A catheter according to claim 6, wherein said mensuration passage in said distal catheter section is shut off for measuring bladder pressure by means of a pressure sensor having an end surface located adjacent said lateral catheter perforation.

* * * * *